United States Patent [19]
Glans et al.

[11] Patent Number: 5,118,805
[45] Date of Patent: Jun. 2, 1992

[54] PHOSPHOROUSTRISLACTAMS AND METHODS FOR THEIR PRODUCTION

[75] Inventors: Jeffrey H. Glans, Somerville; Murali K. Akkapeddi, Morristown, both of N.J.

[73] Assignee: Allied-Signal Inc., Morris Township, N.J.

[21] Appl. No.: 688,773

[22] Filed: Apr. 22, 1991

Related U.S. Application Data

[63] Continuation-in-part of Ser. No. 542,498, Jun. 25, 1990, abandoned.

[51] Int. Cl.$^5$ ............................................. C07F 9/08
[52] U.S. Cl. ................................. 540/451; 540/480; 540/481; 540/487; 540/542; 546/21; 546/25; 525/397
[58] Field of Search ............... 540/487, 542, 480, 481, 540/451; 546/21, 25

[56] References Cited

U.S. PATENT DOCUMENTS
4,927,881  4/1988  Brown ............................................. 52/50

FOREIGN PATENT DOCUMENTS
| | | |
|---|---|---|
| 0142294 | 5/1985 | European Pat. Off. . |
| 2043970 | 3/1971 | Fed. Rep. of Germany ...... 540/487 |
| 86/01572 | 2/1987 | PCT Int'l Appl. ................. 525/394 |
| 87/01027 | 12/1987 | PCT Int'l Appl. ................. 525/391 |

OTHER PUBLICATIONS
Soviet Inventions Illustrated, Sec. CH Week 8423, Jul. 18, 1984, Derwent Publications.

*Primary Examiner*—Robert T. Bond

[57] ABSTRACT

Novel compositions of phosphoroustriscaprolactams, including tris(caprolactyl)phosphite which may be produced in accordance with the methods disclosed, finding particular utility as catalysts for esterification and other condensation reactions.

11 Claims, No Drawings

PHOSPHOROUSTRISLACTAMS AND METHODS FOR THEIR PRODUCTION

REFERENCE TO RELATED APPLICATIONS

The present application is a continuation-in-part application of U.S. patent application Ser. No. 542,498 filed Jun. 25, 1990, now abandoned. The present application is related to U.S. patent application Ser. No. 562,355 filed Aug. 3, 1990, now U.S. Pat. No. 5,037,897.

BACKGROUND

1. Field of the Invention

The invention relates to a novel class of chemical compositions, phosphoroustrislactams, particularly, phosphoroustriscaprolactam, and processes for their preparation.

2. Description of the Prior Art

Engineered plastics comprising so called "blended polymers" find widespread use in industry. Typically these materials comprise two or more constituent materials, such as a two or more polymers, or a polymer with a non-polymeric material, which are form compositions which should ideally exhibit the beneficial features of the several constituents, without any detrimental qualities. Unfortunately, as is well known to the art, blended polymeric materials are rarely attained which offer the desirable characteristics of the constituents, without simultaneously suffering from some detrimental quality. Examples of such useful classes of materials include the polyamides which exhibit good solvent resistance, hydrolytic stability, abrasion resistance and generally good mechanical strength, but are also notoriously poor materials for use in aqueous or humid environments due to high water absorptivity, and poor creep performances at common temperatures. Also, are polyalkylene terephthalates, particularly polyethylene terephthalate ("PET") and polybutylene terephthalate ("PBT") which, due to their crystalline structure, feature useful mechanical properties and are dimensionally stable, but also suffer low glass transition temperatures, "$T_g$" and hence suffer low heat distortion temperatures. A further class of materials include the class of materials referred to as polyphenylene ethers ("PPE"), also interchangeably referred to in the art as polyphenylene oxides ("PPO") which exhibit higher glass transition temperatures, but suffer poorer melt processability and solvent resistance properties than polyalkylene terephthalates. Blends of polyalkylene terephthalate and PPE lact compatibility and hence exhibit poor properties and require a compatibilizing agent to improve their properties. In general, several approaches are known to the art, including the formation of copolymers with other constituents through the use of reactive agents have been proposed in the art in order to improve the compatibility and property improvements in blended polymers, such as that described in European Patent Application 0 129 825 wherein compositions of polyphenylene ethers and polyamides are blended in the presence of an organic phosphate which acts to compatabilize the composition and improve the flame retardant characteristics thereof. U.S. Pat. No. 4,532,306 to Sugio et al. describes compositions comprising a polyphenylene ether resin and a poly(epsilon-caprolactone). Particular constituents which have been proposed in the art to be useful in the formation of improved compositions include that of U.S. Pat. No. 3,862,262 to Hendrick et al. for "Lactam-PolyolAcyl Polylactam Terpolymers" which describe novel terpolymers which find particular use blend formulations, as well as the compositions described by Y. Akiyama in Japanese Patent Application No. 18092-1962, filed May 9, 1962 by Asahi Kasei Kogyo K.K. for a "Method of Polymerizing Pyrrolidone". The limitations of the various classes of polymers and the desirability of forming improved polymer blends indicates a continuing need in the art for novel constituents and compositions which find use as effective compatibilizers in the formation of improved polymer blend compositions, and which provide beneficial effects which have been hitherto unknown to the art.

SUMMARY

In one embodiment, the present invention is directed towards a novel class of compositions, namely "phosphoroustriscaprolactams" according to the general formula

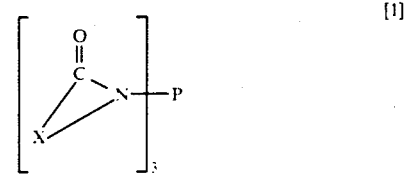

[1]

or the formula [2].

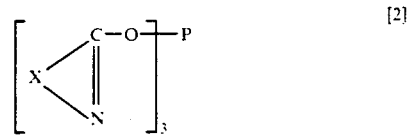

[2]

where X represents a chain of $CH_2$ monomer repeat units of at least 4 and including up to 11 $CH_2$ monomer repeat units.

A further aspect of the invention is a process for the production of these novel compositions.

A still further aspect of the invention is a phosphoroustriscaprolactam wherein the number of $CH_2$ monomer repeat units is 5 and which may be represented by the following formula [3],

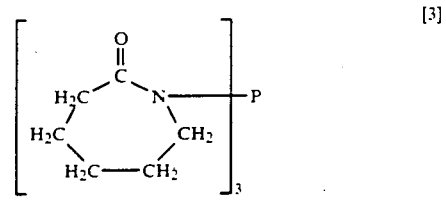

[3]

and a process for its production.

A further aspect of the invention is the production of the novel compounds by a method which includes reacting a lactam and a phosphorous trihalide in the presence of a base in an inert solvent.

A yet further aspect of the present invention is the use of the phosphoroustrislactams in blends comprising a polyphenylene ether, or a polyester, or a polycarbonate.

DESCRIPTION OF THE PREFERRED EMBODIMENTS

In accordance with the invention, the novel phosphoroustriscaprolactams include those being generally represented by formula [1] set forth above, where X represents a chain of $CH_2$ monomer repeat units of 4 to 11 carbon atoms, and more particularly includes the novel composition of phosphoroustriscaprolactams as generally represented by the formula [3] noted above. In the preparation of these novel compounds, suitable lactams include 2-piperidone, caprolactam, and laurolactam. Of these the preferred lactams include caprolactam and piperidone, and of these, the most preferred is caprolactam.

A further constituent necessary is a phosphorous trihalide, a material which is generally represented by the following formula [4].

[4]

where Y is selected from among chlorine, bromine, fluorine and iodine. These phosphorous trihalides are known to the art and may be produced by adding one or more of the halogens, such as bromide to a stirred suspension of red phosphorous in carbon tetrachloride, as is described at pg. 873 of "Reagents for Organic Synthesis" by L. Fieser and M. Fieser, published by John Wiley & Sons, 1967. Of these materials, phosphorous trichloride is preferred.

In one method of production, these constituents should be combined in any proportion to assure that the halogens are substituted during the reaction, which is normally achieved by assuring an excess of the lactams. This is to mean, that for each mole of the phosphorous trihalide reacted, at least 3 moles of a suitable lactam should be used, so to assure that each of the three halogens on each phosphorous trihalide molecules is substituted by a lactam. Accordingly, the mole ratio of the lactam to the phosphorous trihalide is preferably at least 3:1.

The phosphorous trihalide and the lactam may be reacted in the presence of an organic base solution, such as triethylamine in tetrahydrofuran, or other aprotic solvents such as dioxane, glyme, diglyme, and the like to form a solution, suspension, or a dispersion. Generally, the use of tetrahydrofuran is preferred due to the ready availability of this material, and that it may be readily removed by a stripping operation during subsequent isolation.

The reaction may take place at room temperature, i.e., approximately 20 deg. C and throughout the reaction the reaction mixture should be maintained in the temperature range of 5-30 degrees C. It has been found that the reaction is exothermic, and this may require the use of a cooling means which is appropriate to the conditions of the reaction whether such reaction is performed in small quantities, i.e., laboratory benchtop, or in a large size commercial reaction vessel. Accordingly, it is recognized that such suitable cooling means may be an ice bath, water bath, cooling mantle, or suitable method of limiting any temperature rise during the reaction. It has also been recognized that the amount of heat is proportional to the rate of addition of the phosphorous trihalide and it is evident that the rate of addition may be accordingly adjusted to assure that the temperature rise is not excessive and remains within a preferred temperature range of 5-25 deg. C.

In order to prevent oxidation and moisture absorption of the reaction mixture, the reaction mixture should be kept in the presence of an inert gas, such as nitrogen.

Further, the reaction mixture should be well stirred to assure homogeneous distribution of the constituents throughout the reaction process. A stirring means, such as commonly used paddle agitator is a preferred means.

A general method of producing the novel phosphoroustriscaprolactams of the present invention is as follows. Measured amounts of the lactam may be introduced to the organic base solution using standard laboratory glassware, such as a three-necked flask wherein an inert gas may be introduced, preferably nitrogen. The reactants are well mixed through mechanical agitation means, and maintained at room temperature, i.e. approximately 20 deg. C. Afterwards, the phosphorous trihalide is added in a dropwise manner into the flask at a rate sufficiently slow to assure that there is no overheating of the reaction mixture, and that the mixture remains at about 20 deg. C. After all of the phosphorous trihalide has been added, the reaction mixture is stirred without the addition of any other constituent for a period sufficient to assure the complete consumption of the phosphorous trihalide, and the success of the reaction. It is to be recognized that the rate of the reaction is dependent upon the rate of addition, which also controls the heat of the reaction. What this is to mean is that if the reaction mixture may be kept cool by satisfactory cooling means, and assuming that thorough stirring is provided, the rate of the reaction is approximately equal to the time required to add the phosphorous trihalide to form the reaction mixture, and thus determines a minimum time of required. Optionally, to assure thorough mixing of the reactants, the reactants may be retained in the reaction vessel and subjected to further stirring for a period approximately equal to the time used to add the phosphorous trihalide.

Subsequently, water at room temperature sufficient to cause the formation of two phases is added to the reaction mixture, which is continually stirred. Afterwards, the aqueous and the organic phases were separated by any well known technique, including the use of a common separatory funnel. The aqueous phase is discarded, and the organic phase was washed several times with a 10% $K_2CO_3$ solution, and then filtered to separate the solid formed during the reaction. Subsequently, the filtered solid is then washed with a solvent, such as tetrahydrofuran, and dried. Optionally, the filtered solid is vacuum dried over a drying agent such as $P_2O_5$ to assure removal of any traces of the aqueous or organic solvents. In the drying operation, any suitable apparatus may be used, i.e., for small amounts a laboratory drying vessel, for large scale production, a rotary dryer may be utilized being more appropriate.

The resulting solid material is generally white in appearance, and may be recovered as small particles or flakes, or alternatively as a solid mass. Surprisingly, the inventors have found that the novel phosphoroustriscaprolactam compositions are relatively more hydrolytically stable, relative to known materials which are similar in chemical structure, such as phosphorous(tris)pyrrolidone, and related compounds which are known to be highly unstable in the presence of moisture or water, although such materials may be considered to be similar in chemical structure. This feature of the present invention is evidenced by the use of an aqueous wash in the method of producing the novel compositions, a distinguishing feature which allows for the use of these compositions under conditions which could not be served by similar compounds due to their hydrolytic instability. This feature of the present invention is also evidenced by their recoverability after such an aqueous wash in a dry form, such as a powder.

The phosphoroustrislactams of the present invention find use as compatibilizers for blends of thermoplastic resins, including blends comprising a polyphenylene ether and one or more polyesters. In preferred embodiments, the phosphoroustrislactams of the present invention are used in blends comprising: a polyphenylene ether, a polyester, and a functionalized elastomer, and/or an elastomeric polymer.

By way of illustration, and not by limitation, suitable phenol compounds useful for the derivation of PPE therefrom include those represented by the following formula:

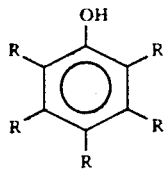

wherein each R is representative of a monovalent substituent selected from the group consisting of hydrogen, halogen, aromatic hydrocarbon, aliphatic hydrocarbon, as well as hydrocarbonoxy radicals which are free of a tertiary alpha carbon atom and halohydrocarbon and halohydrocarbonoxy radicals free of a tertiary alpha-carbon atom and which comprises as least two carbon atoms between the halogen atom and the phenyl nucleus, and wherein at least one R is hydrogen.

Preferred polyphenylene ethers include those of the following general formula:

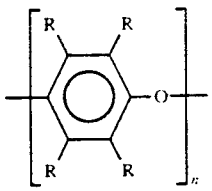

wherein n has a value of 50 or in excess thereof, and R is consistent with the definition given above.

By means of example and not by way of limitation, several polyphenylene ethers suitably represented by the above formula include:
poly(2-ethyl-6-ethoxy-1,4-phenylene)ether,
poly(2-methoxy-6-ethoxy-phenylene)ether,
poly(2,6-dilauryl-1,4-phenylene)ether,
poly(2,6-dibromo-1,4-phenylene)ether,
poly(2,6-diphenyl-1,4-phenylene)ether,
poly(2,6-diethoxy-1,4-phenylene)ether,
poly(2-ethoxy-1,4-phenylene)ether,
poly(2,6-dimethoxy-1,4-phenylene)ether,
poly(2-methyl-6-phenyl-1,4-phenylene)ether,
poly(2,6-dichloro-1,4-phenylene)ether,
poly(2-chloro-1,4-phenylene)ether,
as well as other similar compositions not specifically delineated here.

Polyesters which find use with the present invention include thermoplastic polyester resins which are characterized in exhibiting an intrinsic viscosity of 0.3 to 1.0 dl/g when measured in a 60/40 weight percent mixture of phenol/tetrachlorathene and which further include carboxyl or hydroxyl terminal end groups. Optionally, the end groups may be partially capped, such as through the use of a monoester.

Thermoplastic polyester resins which are preferred for use in conjunction with the instant invention are poly(alkylene terephthalate) resins, including poly(ethylene terephthalate), poly(butylene terephthalate), poly(tetramethylene terephthalate), poly(arylene terephthalate) and copolymers and/or mixtures thereof. As is known to the art, these polyester resins may be obtained through the polycondensation of terephthalic acid, or a lower alkyl ester thereof, and an alkylene diol. By way of example, polyethylene terephthalate or polybutylene terephthalate may be produced by polycondensation of dimethyl terephthalate and ethylene glycol, or 1,4-butane diol after an ester interchange reaction.

Various optional ingredients may also be incorporated as constituents into blends in accordance with the present invention in order to impart further specific properties thereto. The use of one such additive, which is a constituent preferentially utilized, is a material which is used to decrease the crystallinity of the polyester component. Examples of such materials include homopolymers and/or copolymers of polycarbonates and polyestercarbonates. Examples of polycarbonate containing polymers and polycarbonates, and polyestercarbonates include but are not limited to poly(methane bis(4-phenyl)carbonate), poly(1,1-ethane bis(4-phenyl)carbonate), poly(2,2-propane bis(4-phenyl)carbonate), poly(1,1-butane bis(4-phenyl)carbonate, poly(2,2-butane bis(4-phenyl)carbonate), poly(1,1-(1-phenylethane) bis(4-phenyl)carbonate), poly(dipenylmethane bis(4-phenyl)carbonate) which can be obtained from commercial sources or prepared by known techniques. Examples of such commercially available materials include the family of polycarbonate materials marketed by the General Electric Co. under the trade name Lexan ®. Further examples of useful polyester carbonates and methods for their production are described in U.S. Pat. Nos. 4,156,069, 4,386,196 and 4,612,362. Such carbonate containing polymers function in reduction of the crystallinity of the polyester component. In accordance with the teaching of the instant invention, any amount of such carbonate containing polymers which is found to satisfactorally reduce the crystallinity of the polyester component may be used. However, the amount of carbonate containing polymer added is usually from about 5% to about 40% by weight based on the total weight of the polyester, and is preferably from about 5% to about 35% by weight of the polyester, and most preferably between 5% to about 25% by weight of the polyester.

In preferred embodiments of the invention, a polymer exhibiting elastomeric properties may be included where the inclusion of such a polymer provides a beneficial effect upon the impact resistance of materials formed from such a blend. Throughout this specification and the claims, the term "functionalized elastomer" is meant to be understood as the polymer exhibiting elastmeric properties and provide a beneficial effect upon the impact resistance of materials as described hereinafter. Such an elastomeric polymer is defined as having an ASTM D-638 tensile modulus of less than about 40,000 psi (276 MPa), and preferably less than about 20,000 psi (138 MPa). Examples of such elastomeric polymers may be block, graft or random copolymers, and can be made of reactive monomers which comprise part of the polymer chains, or grafted, or as branches of the polymer. Some examples of such reactive monomers include dienes, unsaturated carboxylic acids, as well as derivatives thereof, including esters and anhydrides as well as unsaturated epoxide moiety containing constituents. By way of illustration, but not by way of limitation, examples of such useful elastomeric polymers include α-olefin containing copolymers, especially ethylene copolymers, copolymers containing acrylic acid salts, known to the art as "acrylic acid ionomers" which include by way of illustration ethylene/methacrylic acid neutralized with sodium, ethylene/maleic anhydride, ethylene/ethyl acrylate, ethylene/glycidyl methacrylate, ethylene/methyl methacrylate and the like. Further examples of elastomeric polymers include natural rubber, nitrile rubber, polyacrylates, butadiene polymers, isobutylene/isoprene copolymers, styrene/ethylene/propylene/diene copolymers, acrylonitrile/styrene/diene copolymers, ethylene/styrene/diene copolymers, butadiene/styrene copolymers, styrene/butadiene/styrene copolymers, acrylonitrile/butadiene/styrene copolymers, acrylic core shell rubbers such as:

methyl methacrylate/butadiene/styrene graft copolymers, polyalkylene oxide elastomers, poly(dimethyl siloxane) rubbers, and the like. poly(chloroprene), acrylonitrile/butadiene copolymers, poly(isobutylene), isobutylene/butadiene copolymers, ethylene/propylene copolymers, polyneoprene, ethylene/propylene/butadiene copolymers, as well as wholly or partially hydrogenated, oxidized or carboxylated derivatives. Useful elastomeric polymers can include monomeric units derived from aromatic vinyl monomers, olefins, acrylic acid, methacrylic acid, and their derivatives. These materials may be obtained from commercial sources or produced through techniques known to the art. Further examples of useful elastomeric polymers and methods of their production are described in U.S. Pat. Nos. 4,315,086 and 4,175,358. Preferred elastomeric polymers (also known to the art as "rubbers" or "rubbery polymers") are carboxylated or epoxide moiety containing elastomers, including those which are reaction products of rubber with anhydrides, and include maleic anhydrides: reaction products of rubber with glycidyl methacrylates, and subsequent oxidation as may be effected by the use of a permanganate; grafting reactions of the double bonds of unsaturated monomers having pendant carboxylic acid functions such as acrylic acid, methacrylic acid, and the like. Particularly preferred rubbers include maleated rubbers, especially where the rubbers are simple triblock copolymers of the "A-B-A" structure, or are multiblock copolymers of the "[AB]$_n$" linear or radial type, where "n" is any integer between 2 and 10 inclusive, "A" is representative of a block derived from a polyvinylaromatic monomer such as styrene or vinyl toluene, and "B" is a block derived from a conjugated diene monomer as well as hydrogenated derivatives thereof. Many of these elastomers are commercially available under the trade name Kraton ® from Shell Chemical Co.

The elastomeric material functions to improve the impact resistance of blends according to the invention, and the amount of elastomeric material added may be any amount which provides such an impact resistance improvement to the blend. Based on the weight of the polyester and the polyphenylene ether, the elastomeric material is present in an amount of between 2.5% and 25%, preferably in an amount between 3% and 18% inclusive, and most preferably form about 5% and 15% by weight on the aforementioned basis.

Other optional constituents which may be incorporated into the blends according to the instant invention include such materials as fillers, impact modifiers, dyes, colorants, pigments, plasticizers, mold release agents, fire retardants, drip retardants, antioxidants, UV stabilizing agents, mold release agents, colorants, antistatic agents, nucleating agents, thermal stabilizing agents, and the like. These optional constituents may be added to the mixture at any appropriate time during the production of the blend, and as they are well known to the art, are not here described with particularity. All of these optional constituents are commercially available. The compositions according to the instant invention may be made by any technique or process, presently known yet to be developed which will effect an intimate blending of the constituents of the compositions, particularly the PPE, polyester and the phosphorous-trislactam. By way of example, such useful methods include formation of a solution in which the constituents are dissolved, suspended or dispersed in a suitable solvent, after which the solvent is removed from the resultant blend composition by conventional processes in order to form compositions in accordance with the teachings of the instant invention. An alternative technique is by the dry-blending the constituents in a dry particulate form, such as powders, pellets, flakes, prills or the like, and then heated to a temperature equal to or greater than the melting point of either the PPE or the polyester. A further variation on this technique which may be utilized where all of the desired constituents are not available in powder form, is an additional process steps of mixing any liquid constituents or constituents in liquid form, subsequent to dry blending of the constituents, and thoroughly mixing the constituents, as well as removal of excess liquids during processing by well known techniques.

During production of compositions according to the instant invention, it is recognized that acceptable temperatures used in heating the constituents may vary over a wide range, and is dependent upon the constitution of the any particular blend composition.

Preferably, the temperature should be at least as high as the melting point of the polyester and the PPE but at the same time, should not be as high as the degradation temperatures of either the PPE or the polyester. In particularly preferred embodiments, the temperature is such that the polyester and PPE will be retained in a molten state sufficiently long to allow for the phosphoroustrislactam to react with either the polyester or PPE and form a block or graft copolymer therewith.

The foregoing invention will be more apparent by reference to specific embodiments which are representative of the invention. It is nonetheless to be understood that the particular embodiments described herein are provided for the purpose of illustration, and not be means of limitation, and that it is to be further understood that the present invention may be practiced in a manner which is not exemplified herein without departing from its scope.

EXAMPLES

Example 1

Into a dry, 2 liter three-necked flask fitted with a mechanical stirrer, a reflux condenser, and a nitrogen sweep was placed 98.1 grams (0.867 mol) of freshly distilled caprolactam, 128 ml (0.918 mol) of triethylamine, and 600 ml of dry tetrahydrofuran. To this solution was in a dropwise manner added 25.2 ml (0.286 mol) of phosphorus trichloride at a rate slow enough to prevent the overheating of the flask and its contents above 25 deg. C. During the addition of the phosphorus trichloride a voluminous white precipitate was noted to form. The reaction mixture was stirred at room temperature for three hours after which was added 200 ml of water with stirring.

Afterwards, the resulting suspension was transferred to a two liter separatory funnel to separate the organic phase of the suspension from the inorganic phase. The recovered organic phase which contained the white precipitate was thrice washed with water, then a 10% $K_2CO_3$ aqueous solution, and filtered to recover the white precipitate. The filtered, recovered white precipitate was washed with tetrahydrofuran (THF) at approximately 20 deg. C. and dried over $P_2O_5$ in a vacuum overnight to provide a yield of 86.6 grams of the white solid, which was determined to be a 82% yield.

Example 2

Into a dry 250 ml three necked flask fitted with a mechanical stirrer, a reflux condenser, and a nitrogen sweep was added 10.7 grams (9.45 millimoles) of molten caprolactam, 14.0 ml (10.0 millimoles) of triethylamine, and 100 ml of tetrahydrofuran, all of which was conducted at room temperature. A 40 percent solution of 9.0 ml (9.48 millimoles) of phosphorous tribromide in tetrahydrofuran at room temperature was added in a dropwise manner to the contents of the three necked flask, as the contents of the flask were stirred and subjected to the nitrogen sweep. Upon the consumption of the solution of phosphorous tribromide in the tetrahydrofuran, the contents of the flask were subjected to further stirring for several hours, after which 20 ml of water was added slowly to the flask and stirring continued for an additional period of ten minutes. The contents of the vessel were then withdrawn from the vessel and filtered and washed twice with tetrahydrofuran at room temperature, and subsequently washed twice with diethyl ether at room temperature to yield 11.9 grams of a white solid, which was calculated to be a 81% yield.

Example 3

Into a dry 250 ml three necked flask fitted with a mechanical stirrer, a reflux condenser, and a nitrogen sweep was added 9.2 grams (813 millimoles) of molten caprolactam, 12.0 ml (86.1 millimoles) of triethylamine, and 100 ml of diethyl ether, all of which was conducted at room temperature. A 10% solution of 2.7 ml (3.1 millimoles) of phosphorous trichloride in diethyl ether at room temperature was added in a dropwise manner to the contents of the three necked flask, as the contents of the flask were stirred and subjected to the nitrogen sweep. Upon the consumption of the solution of phosphorous trichloride in the diethyl ether, the contents of the flask were subjected to further stirring for several hours, after which 20 ml water was added slowly to the flask and stirring continued for an additional period of ten minutes. The contents of the vessel were then withdrawn and filtered and the filtered solid was washed twice with diethyl ether at room temperature to yield 10.5 grams of a white solid, which was calculated to be a theoretical yield of 105% yield. The filtered solid material contained residual triethylamine hydrochloride.

Example 4

Into a dry 250 ml three necked flask fitted with a mechanical stirrer, a reflux condenser, and a nitrogen sweep was added 99.5 grams (1.01 mol) of molten caprolactam, and 800 ml of chloroform. To this was subsequently provided 150 ml (1.08 mol) of triethylamine, all of which was conducted at room temperature. A concentrated solution of 26.5 ml (0.304 mol) of phosphorous trichloride in chloroform at room temperature was added in a dropwise manner to the contents of the three necked flask, as the contents of the flask were stirred and subjected to the nitrogen sweep during which a homogeneous orange solution was observed to form. Upon the consumption of the solution of phosphorous trichloride solution, the contents of the flask were subjected to further stirring for two hours, after which the solution was washed three times, each time using 1 liter of water at room temperature, then twice with 500 ml of an aqueous 10% $K_2CO_3$ solution, then 10 grams of $MgSO_4$ was added to dry the composition, and then the composition was reduced by the use of a rotary evaporator. After most of the chloroform (approximately 90%) was removed, approximately 1000 ml of diethyl ether at room temperature was added. The contents of the vessel were then withdrawn and filtered, and the filtered solid was washed with diethyl ether at room temperature to yield 64.6 grams of a white solid, which was calculated to be a theoretical yield of 58%.

Examples 5-8

Examples 5-8 illustrate the use of the phosphorous-trislactams as compatibilizing agents in thermoplastic blends.

For each of the following examples, the poly(ethylene terephthalate) used exhibited an intrinsic viscosity of 0.3 to 1.0 dl/g when measured in a 60/40 weight percent mixture of phenol/tetrachlorathene. The poly(phenylene ether)s, or PPEs used were used as described below, and the phosphorous triscaprolactam used was the reaction product of caprolactam and phosphorous trichloride.

Example 5

For forming Examples 5, a mixture of 48.5 parts of PET, and 48.5 parts of PPE having, having an intrinsic viscosity of 0.36 as measured in chloroform, were tumble blended together in a sealed container with 3 parts of phosphorous triscaprolactam. Afterwards, each of the mixtures were supplied to the feed hopper placed at the throat of a Killion 1 inch single screw extruder. The extruder barrel had a length to diameter ratio of 30 to 1, and the zones of the barrel were heated to the following temperatures: zone 1, 400 deg. F., zone 2, 500 deg. F., zone 3, 510 deg. F., zone 4, between 520-550 deg. F. The extruder included an injection port located 15.5 inches from the throat of the screw and immediately preceeding a high-compression zone, which zone has a length of 8 inches, and the extruder also included a vacuum port located near the die. The first exit die was maintained at a temperature of 530 degrees F, and the second die was maintained at a temperature of between 480-510 deg. F. The extruder was outfitted with a 2 stage Maddock screw, and throughout the extrusion the rotational speed of the screw was maintained at a constant of 50 RPM. The extrudate exiting the die was in the form of strands having a diameter of ¼ inch, and were quickly passed into a water bath to quench and cool the strands. The mass output of the extruder was determined to be 39 grams/minute. The strands were subsequently pelletized to form a feed stock useful for injection molding. The extrudate so formed was noted to be amber in color. A portion of the pellets so formed was removed, ground to form a fine powder and exhaustively extracted in chloroform in order to remove as much as possible of the unreacted PPE remaining in the extrudate. The resulting powder was dried in a vacuum.

The amount of the extractable PPE which was determined for each of the compositions provided an indicator of the relative amount of reacted PPE resulting from the extrusion process.

For the production of a film, the respective compositions which were ground in a mill through a 2 mm screen and dried overnight at 110 deg. C, and afterwards were placed on the Teflon ® coated side of a sheet of aluminum foil of thickness 0.003 inch. A preheated steel plate at approximately 280 deg. C and having dimensions of 8 inches by 8 inches were used to underlay the non-coated side of the aluminum foil sheet bearing the powder was leveled and then a similar second piece of Teflon ® coated aluminum foil was placed on the powder so that the powder was contained between the two Teflon ® faces of the two aluminum foil sheets. A second preheated steel plate of like dimensions and at approximately 280 deg. C was layered in register on the non-Teflon ® coated side of the second sheet of aluminum foil to form a sandwich structure after which the sandwiched structure was inserted into the heated Wabash molding press which throughout the molding operation was maintained at 280 deg. C. After 60 seconds of contact pressure, that is to say 0 psig, the pressure was gradually and continuously increased to 5 tons over a period of 30 seconds in order to improve the flow of the powder. Afterwards, at 90 seconds after the original insertion of the sandwiched structure, the pressure was increased to 50 tons, and there maintained for 90 seconds. Afterwards, the entire assembly was removed and transferred to cooling platens and there maintained under a pressure of 50 tons for a period of between 7-8 minutes. Afterwards, the sandwiched structure was disassembled, and the film structure formed by the compression operation was recovered.

For performing physical testing of the material, the compression molded structures noted above were cut into "Type" 4 bars, which were subsequently tested to determine their tensile properties according to ASTM-D 638.

Physical testing of the material formed in Example 5 featured the following results: tensile strength: 5.8 kpsi, tensile modulus, 406 kpsi, elongation, 1.6%, extractable PPE, 39%.

Example 6

A composition comprising 38.5% of a polyphenylene ether having the characteristics of; Wt.Avg.Mol.Wt. (Mw) of 34800, No.Avg.Mol.Wt. (Mn) of 4800, an intrinsic viscosity (IV) of 0.30, 38.5% of a poly(ethylene terephthalate) having an intrinsic viscosity of 0.7, 10% of a polycarbonate resin which is commercially available from the General Electric Co. under the designation Lexan ® 101, 10% of a Kraton ® rubber, an elastomeric constitutent which is commercially available from Shell Chemical Co. under the trade designation "K-FG 1901X" and 3% of a phosphorous triscaprolactam was provided to the Killion 1 inch extruder and processed to form strands under the conditions of, and in the manner used to form the articles according to Examples 1-4 recited above. The extrudate was injection molded to form Type 2 tensile test bars in accordance with ASTM D-638 requirements and physical testing yielded the following results: repeated notched Izod test of 1.4 ft-lb/in., a tensile modulus of 259 kpsi, a tensile strength of 6.1 kpsi, and an elongation of 23% at break.

Example 7

A blend of 49 parts by weight of a poly(phenylene ether) having an intrinsic viscosity of 0.36 as measured in chloroform, 49 parts by weight of poly(ethylene terephthalate) were tumble blended together in a sealed container with 2 parts by weight of phosphorous triscaprolactam. Afterwards, each of the mixtures were supplied to the feed hopper placed at the throat of a Killion 1 inch single screw extruder outfitted with a two-stage Maddox screw. The extruder barrel had a length to diameter ratio of 30 to 1, and the zones of the barrel were heated to the following temperatures: zone 1, 500-480 deg. F., zone 2, 480 deg. F., zone 3, 500 deg. F., zone 4, between 500-520 deg. F. The extruder included an injection port located 15.5 inches from the throat of the screw and immediately preceeding a high-compression zone, which zone has a length of 8 inches, and the extruder also included a vacuum port near the die. The vacuum port was operated to draw a vacuum approaching 0 mm of mercury. The first exit die was maintained at a temperature of 520 degrees F, and the second die was maintained at a temperature of between 470-540 deg. F. The extruder was outfitted with a 2 stage Maddock screw, and throughout the extrusion the rotational speed of the screw was maintained at a constant of 52 RPM, and the motor drew 5.0 amperes of current to maintain a throughput rate of 22 grams per minute of extrudate. The extrudate exiting the die was in the form of strands having a diameter of ¼ inch, and were quickly passed into a water bath to quench and cool the strands. The strands were subsequently pelletized to form a feed stock useful for injection molding. The extrudate so formed was noted to be amber in color. A portion of the pellets so formed were removed, ground to form a fine powder and exhaustively extracted in chloroform in order to remove as much as possible of the unreacted PPE remaining in the extrudate and to determine the amount of extractable PPE in the pelletized extrudate, which was then dried in a vacuum.

The pelletized extrudate was afterwards injection molded to form test bars in accordance with ASTM D-638 specifications. The extruder used was an Arburg Injection molding machine, which was maintained to have a melt temperature of 180 deg. F., and which was set to have the following barrel temperatures: First barrel temperature, 285 deg. C., second barrel temperature, 285 deg. C., third barrel temperature, 280 deg. C. The screw speed was set at 200, with the screw motor set at 18.0 The boost pressure was 1100 psi, the holding pressure 400 psi. For the molding operation, a shot size of 7 lbs was used, and the following times were used: injection time of 0.06 sec, a holding time of 15.0 sec, a cooling time of 10.0 seconds, and a mold open time of 2.5 sec. The sampled molded were noted to need no additional mold release agents for their removal, showed no warpage on cooling and evidenced no delamination. The physical property testing yielded the following results: tensile strength, 9.6 kpsi; tensile modulus, 333 kpsi, percent elongation, 3.8%.

Example 8

A blend composition consisting of 49 parts by weight of a preblended mixture formed by coextruding a blend of PPE and Kraton ® FG 1901x (having a ratio of PPE: Kraton ® of 80:20), 10 parts by weight of a poly(carbonate) (Lexan ® 101), 39 parts by weight of poly(ethylene terephthalate) and 2 parts by weight of phosphorous triscaprolactam were supplied to the feed hopper placed at the throat of a Killion 1 inch single screw extruder outfitted with a two-stage Maddox screw as described in conjunction with Example 6. The zones of the barrel were heated to the following temperatures: zone 1, 500-460 deg. F., zone 2, 480 deg. F., zone 3, 500 deg. F., zone 4, between 500-520 deg. F. The extruder included an injection port located 15.5 inches from the throat of the screw and immediately preceeding a high-compression zone, which zone has a length of 8 inches, and the extruder also included a vacuum port near the die. The vacuum port was operated to draw a vacuum approaching 0 mm of mercury. The first exit die was maintained at a temperature of 520 degrees F. and the second die was maintained at a temperature of between 420-540 deg. F. The 2 stage Maddock screw was maintained at a rotational speed of 52 RPM, and the motor drew 4.5 amperes of current to maintain a throughput rate of 50 grams per minute of extrudate. The extrudate exiting the die was in the form of strands having a diameter of ¼ inch, and were quickly passed into a water bath to quench and cool the strands. The strands were subsequently pelletized to form a feed stock useful for injection molding. The extrudate so formed was noted to be amber in color. A portion of the pellets were removed, ground to form a fine powder and exhaustively extracted in chloroform in order to remove as much as possible of the unreacted PPE remaining in the extrudate and to determine the amount of extractable PPE in the pelletized extrudate, which was then dried in a vacuum.

The pelletized extrudate was afterwards injection molded to form Type 2 test bars in accordance with ASTM D-638 specifications in the general manner outlined in Example 6 above, and afterwards the samples so formed were subjected to physical testing. The results of physical testing included the following: tensile strength, 607 kpsi; tensile modulus, 247 kpsi; percent elongation, 36.6%.

It will be appreciated that the instant specifications and examples set forth herein are by way of illustration and not limitation, and that various modifications and changes may be made without departing from the spirit and scope of the present invention, whose limitations are bounded only by the appendant claims.

What we claim is:

1. A compound according to the formula:

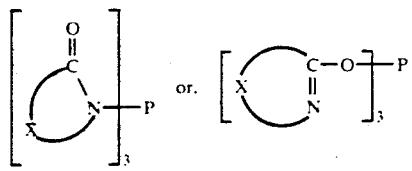

where X represents a chain of $CH_2$ monomer repeat units of at least 4 and including up to 11 $CH_2$ monomer repeat units.

2. The compound of claim 1 wherein the number of $CH_2$ monomer repeat units is 5 and which may be represented by the formula

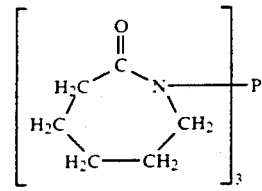

3. The compound of claim 1 wherein the number of $CH_2$ monomer repeat units is 11.

4. A process for producing the compound according to claim 1 which consists of the process steps of:
reacting a lactam selected from the group consisting of 2-piperidone, caprolactam and laurolactam and a phosphorous trihalide which may be generally represented by the formula;

and where Y is selected from among the group consisting of: fluorine, bromine, iodine and chlorine in the presence of triethylamine in aprotic solvents including dioxane, glyme, and diglyme or in an inert solvent selected from the group consisting of tetrahydrofuran, diethyl ether, and chloroform.

5. The process of claim 4 wherein
the lactam is combined with the phosphorous trihalide in a proportion of at least 3:1.

6. The process of claim 4 which further includes the process step of:
cooling the reaction mixture comprising the lactam and the phosphorous trihalide in the presence of the base in the inert solvent.

7. The process of claim 4 which further includes the process step of:
adding water to the reaction mixture comprising the lactam and the phosphorous trihalide.

8. The process of claim 4 which further includes the process step of:
washing the product of the lactam and the phosphorous trihalide with at least one reagent selected from the group consisting of: water, an aqueous solution of $K_2CO_3$, tetrahydrofuran, diethyl ether.

9. The process of claim 4 which further includes the process step of:
recovering a dry reaction product of the reaction of the phosphorous trihalide and the lactam.

10. The process according to claim 4 which includes the process steps of:
adding the phosphorous trihalide to the lactam in the reaction mixture at a rate sufficient to maintain the temperature of the reaction mixture below about 25 deg. C.

11. The process according to claim 10 which further includes the process steps of:
selectively cooling the reaction mixture to maintain the temperature in the range of 5 and 25 deg. C. throughout the process.

* * * * *